(12) United States Patent
Schwarzbraun

(10) Patent No.: US 8,961,177 B2
(45) Date of Patent: Feb. 24, 2015

(54) MEDICAL OR DENTAL HANDPIECE

(71) Applicant: W&H Dentalwerk Bürmoos GmbH, Bürmoos (AT)

(72) Inventor: Josef Schwarzbraun, Lamprechtshausen (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 0 days.

(21) Appl. No.: 14/155,048

(22) Filed: Jan. 14, 2014

(65) Prior Publication Data
US 2014/0199654 A1 Jul. 17, 2014

(30) Foreign Application Priority Data

Jan. 14, 2013 (EP) .................................... 13151104

(51) Int. Cl.
*A61C 1/07* (2006.01)
*A61C 1/14* (2006.01)
*A61C 1/12* (2006.01)
*A61B 19/00* (2006.01)

(52) U.S. Cl.
CPC . *A61C 1/14* (2013.01); *A61C 1/148* (2013.01); *A61C 1/07* (2013.01); *A61C 1/12* (2013.01); *A61B 19/22* (2013.01)
USPC .......................................... 433/127; 433/114

(58) Field of Classification Search
USPC ................. 433/114, 118, 122, 123, 125, 127
See application file for complete search history.

(56) References Cited

U.S. PATENT DOCUMENTS

| 4,940,410 A | * | 7/1990 | Apap et al. ..................... 433/102 |
| 5,454,718 A | * | 10/1995 | Strohmaier .................... 433/122 |
| 6,030,216 A | * | 2/2000 | Rosenstatter ................. 433/120 |
| 6,488,500 B2 | * | 12/2002 | Rosenstatter ................. 433/120 |

FOREIGN PATENT DOCUMENTS

| EP | 0191574 | 8/1986 |
| EP | 0360161 | 3/1990 |
| EP | 0577981 | 1/1994 |
| EP | 1627611 | 2/2006 |

OTHER PUBLICATIONS

European Search Report for EP13151104 (mailed Jul. 4, 2013).

* cited by examiner

*Primary Examiner* — Ralph Lewis
(74) *Attorney, Agent, or Firm* — Klarquist Sparkman, LLP

(57) ABSTRACT

A medical or dental handpiece which has an outer sleeve, a tool-holding sleeve for holding a treatment tool, wherein the tool-holding sleeve has a central axis about which the tool-holding sleeve can be rotated and wherein the tool-holding sleeve can be induced to a stroke motion by a driveshaft of the handpiece, and an adjusting device, which is designed to secure the tool-holding sleeve selectively in a rotational position or to allow a free rotatability of the tool-holding sleeve, wherein the adjusting device has a fixation element, which secures or releases the tool-holding sleeve and at least one adjusting element, which is at least operatively connected to the fixation element, wherein the adjusting element is movable substantially in parallel with the central axis of the tool-holding sleeve.

19 Claims, 6 Drawing Sheets

MEDICAL OR DENTAL HANDPIECE

CROSS REFERENCE TO RELATED APPLICATION

The present application claims priority from pending European Patent Application No. 13151104.0, filed Jan. 14, 2013, which is incorporated herein by reference.

BACKGROUND

1. Field

The present application relates to a medical or dental handpiece having a tool-holding sleeve for holding a treatment tool, wherein the tool-holding sleeve has a central axis about which the tool-holding sleeve is rotatable and wherein the tool-holding sleeve can be induced to a stroke movement by a driveshaft in the handpiece.

2. Description of Prior Art

Such a medical or dental handpiece is known from Patent Application EP 1 627 611 A1. This handpiece additionally has an adjusting device, which optionally allows free rotatability of the tool-holding sleeve and a tool arranged therein or secures the rotational position of the tool-holding sleeve and the tool arranged therein. For actuating the adjusting device, an actuating element in the form of an elongated slide extending along the handle part of the handpiece is provided.

SUMMARY

It is thus an object of the present application is to create a medical or dental handpiece having a rotatable tool-holding sleeve, which can be induced to a stroke motion and which has an alternative adjusting device whose actuating element in particular does not extend along the handle part of the handpiece.

This object is achieved according to one embodiment by a medical or dental handpiece, comprising: an outer sleeve, a tool-holding sleeve for holding a treatment tool, wherein the tool-holding sleeve has a central axis about which the tool-holding sleeve is rotatable and wherein the tool-holding sleeve can be induced to a stroke motion (along the central axis) by a driveshaft of the handpiece, and an adjusting device, which is designed to optionally secure the tool-holding sleeve in a rotational position or to allow free rotatability of the tool-holding sleeve, wherein the adjusting device comprises a fixation element, which secures or releases the tool-holding sleeve and an adjusting element, which is at least operatively (or, alternatively, permanently) connected to the fixation element, wherein the adjusting element can be moved substantially parallel to the central axis of the tool-holding sleeve.

Due to the adjusting element, which is movable substantially parallel to the central axis of the tool-holding sleeve, it is possible to provide the actuating element for actuating the adjusting device in the axial direction (based on the central axis of the tool-holding sleeve) in relation to the tool-holding sleeve, in particular to provide the actuating element so that it is axially adjacent to the tool-holding sleeve or is concentric around the central axis. The actuating element is preferably provided on a head section of the handpiece in which the tool-holding sleeve is arranged. The actuating element thus no longer extends along the handle part of the handpiece, as is known from the prior art, so that the handpiece can be held better by the user and so that the front end of the handle part, which is especially close to the treatment site does not have any additional structures where soiling, for example, treatment residues such as blood or tissue could adhere.

The tool-holding sleeve is preferably designed as a hollow tubular or elongated sleeve. The tool-holding sleeve is designed for detachable, preferably friction-locking and/or form-fitting connection to a tool. The tool comprises in particular a tool for preparation of teeth, for example, a tool like a file, a tool having a planar abrasive working section, a dental file, a tool with a saw blade or a tool with a working section resembling a saw blade, in particular for removal of enamel.

Preferably different geometric structures, for example, parts of an eccentric gear that induces a stroke motion on the tool-holding sleeve, in particular an eccentric pin or a groove or a ring groove to receive an eccentric pin are provided on the outer surface or on the outer lateral surface of the tool-holding sleeve. In particular preferably at least one, preferably concave recess for receiving at least a part of the fixation element is provided on the outer surface of the tool-holding sleeve, in particular on the contact area with the fixation element. Each recess defines a fixed or predetermined rotational position in which the tool-holding sleeve can be secured when the fixation element engages in the recess. The at least one recess is preferably designed as an elongated groove or channel extending along the outer surface of the tool-holding sleeve, in particular substantially parallel to the central axis of the outer sleeve to permit an easy stroke motion. The axial length of the groove or channel (based on the central axis of the tool-holding sleeve) is, for example, at least equal to the axial height of the groove or ring groove to receive the eccentric pin of the eccentric gear, preferably larger than the axial height of the groove or the ring groove. Alternatively, the outer surface or the outer lateral surface of the tool-holding sleeve in the contact area with the fixation element is designed to be substantially smooth or without a recess to receive a fixation element, so that the tool-holding sleeve can be secured by the fixation element in any desired rotational position or in any rotational angle.

According to an embodiment, the fixation element comprises at least one securing element (form element) being substantially radially movable in relation to the central axis of the tool-holding sleeve and preferably having a spherical or convex end. The fixation element is thus in particular arranged in the handpiece so that it can be moved substantially radially to the tool-holding sleeve and away from the tool-holding sleeve. The fixation element is especially preferably designed as a sphere. Alternatively, the securing element is designed, for example, as a cylinder or pin, preferably with a convex or spherical end directed toward the tool-holding sleeve. Preferably a single fixation element is provided but a plurality of fixation elements, in particular distributed substantially equally around the tool-holding sleeve may be provided alternatively.

The fixation element is preferably accommodated in a guide extending radially to the central axis of the tool-holding sleeve, for example, in a groove or a borehole. The guide supports and secures the fixation element in the handpiece and ensures a reliable radial movement of the fixation element toward and away from the tool-holding sleeve. The guide and in particular the fixation element are preferably provided in the contact area of the fixation element with the tool-holding sleeve, in particular in the axial segment of the tool-holding sleeve, which comprises the recess for receiving the fixation element.

The fixation element is preferably movable between a position contacting the tool-holding sleeve and a position not contacting the tool-holding sleeve. In the contacting position, the fixation element approaches the central axis of the tool-holding sleeve radially. In the contacting position, the fixation element engages in particular in the at least one recess, which preferably has a concave shape, so that the tool-holding sleeve is secured in a defined or predetermined rotational position. In the non-contacting position, the fixation element is radially a greater distance away from the central axis of the tool-holding sleeve than it is in the contacting position. In the non-contacting position, the fixation element in particular does not engage in the at least one recess, which is preferably concave, so that the tool-holding sleeve is freely rotatable about its central axis when a torque is exerted on the tool-holding sleeve and/or a tool accommodated therein.

According to one embodiment, the adjusting element comprises an elongated, preferably rod-shaped element. The adjusting element is preferably designed as a pin. The adjusting element additionally has a longitudinal axis which is arranged substantially parallel to the central axis of the tool-holding sleeve in particular.

The adjusting element is preferably supported or arranged in the handpiece in such a way that it is movable substantially along its longitudinal axis, in particular slidable. The adjusting element is preferably accommodated in a guide, for example, in a groove or a borehole. The guide ensures reliable movement of the adjusting element along its longitudinal axis. A shared guidance element is preferably provided in which the fixation element and the adjusting element are arranged and/or accommodated and/or guided jointly. The borehole or the groove for guiding the adjusting element and the borehole or groove for guiding the fixation element are preferably arranged at approximately right angles to one another in particular in the shared guide element. The guide or the shared guide element is preferably fixedly arranged in the handpiece and the adjusting element and the fixation element are arranged to be movable in relation to the guide element.

According to one embodiment, the adjusting element has different outside diameters along its longitudinal axis, in particular in a contact area with the fixation element. The segments of the adjusting element with different outside diameters are connected to one another by a step or a shoulder on the adjusting element, for example, or by a connecting section of the adjusting element designed obliquely or at an angle to the longitudinal axis. Alternatively, the adjusting element has a steadily changing outside diameter over at least a portion of its length.

The movement of the adjusting element along its longitudinal axis produces or permits the substantially radial movement of the fixation element to or from the tool-holding sleeve based on the operative or direct connection of the adjusting element with the fixation element. The adjusting element is preferably arranged in the handpiece in such a way that by moving the adjusting element, preferably along its longitudinal axis, selectively a first section of the adjusting element with a first outside diameter, for example, a large outside diameter or a second section of the adjusting element with a second outside diameter, for example, a small outside diameter is opposite the fixation element or is operatively assigned to the fixation element. The first outside diameter is preferably of such a dimension that when the first outside diameter is opposite or operatively assigned to the fixation element, then the fixation element engages the recess, which preferably has a concave shape, of the tool-holding sleeve. In particular the first outside diameter is of such a dimension that the first section having the first outside diameter moves or presses the fixation element into the recess, or the fixation element is clamped between the first section and the tool-holding sleeve, in particular the recess. The second outside diameter is preferably of such a dimension that, when the second outside diameter is opposite the fixation element or is operatively assigned to it, then the fixation element does not engage the recess, which preferably has a concave shape, in the tool-holding sleeve or it can be removed from the recess or it can be moved in its guide.

According to one embodiment, the handpiece has a spring element prestressing the adjusting element, preferably a spiral spring. A protrusion or flange on which the spring element is supported is preferably provided on the adjusting element. The spring element, preferably also a part of the adjusting element, is/are arranged in particular in a receptacle or borehole in the handpiece, for example, in a receptacle or borehole in the outer sleeve. The spring element prestresses the adjusting element into a first position in which, for example, the first section of the adjusting element with the first outside diameter is opposite the fixation element so that the fixation element engages the recess, preferably concave in shape, of the tool-holding sleeve. The spring element is further designed so that, by exerting a force counteracting the spring force of the spring element, for example, by means of an actuating element, the shape of the spring element can be altered, for example, compressed, so that the adjusting element can be moved into a second position in which the section of the adjusting element with the second outside diameter is opposite the fixation element, and the fixation element does not engage the recess of the tool-holding sleeve or can be removed from the recess. It is of course also possible to design or arrange the spring element and/or the adjusting element in such a way that the spring element prestresses the adjusting element into the second position and the adjusting element can be moved into the first position by exerting a force counteracting the spring force of the spring element.

According to one embodiment, the handpiece comprises an actuating element for actuating the adjusting device, in particular the adjusting element, that is movable in relation to the outer sleeve of the handpiece, in particular rotatable or pivotable. The actuating element is preferably operatively connected to the adjusting element and in particular the actuating element is designed to move the adjusting element substantially parallel to the central axis of the tool-holding sleeve or along its longitudinal axis. The actuating element is designed as a cap or as a button, for example. The actuating element is preferably designed as part of the outer sleeve of the handpiece and/or is accommodated in an opening in the outer sleeve.

The actuating element is mounted movably, in particular rotatably or pivotably, on the outer sleeve and/or connected to the outer sleeve and/or supported on components of the handpiece that are in turn connected to the outer sleeve, in particular connected to the outer sleeve rotationally fixed or immovably, and/or connected to these components. The components connected to the outer sleeve include, for example, pins which form an axis of rotation or a pivot axis for the actuating element and/or bearing elements, in particular balls on which the actuating element is supported in a movable manner and/or preferable the guide for the adjusting element or the fixation element or the shared guide element of the adjusting and fixation element. Preferably, the bearing elements on which the actuating element is movably supported are arranged on the shared guide element.

According to one embodiment, the handpiece comprises a locking device, which is designed to lock the actuating element or the fixation element at least in the first position described above in which the fixation element engages the recess of the tool-holding sleeve and secures the tool-holding sleeve in a rotational position or in the second position described above in which the fixation element does not engage the recess of the tool-holding sleeve and the fixation element allows a free rotatability of the tool-holding sleeve. The locking device is designed in particular so that it holds or supports the actuating element in the first position and/or in the second position, so that the fixation element engages or does not engage the recess in the tool-holding sleeve. The locking device preferably comprises a first locking part on the actuating element and the second locking part, wherein by moving the actuating element, the first locking part and the second locking part can be moved in relation to one another. The second locking part is in particular provided on a component arranged immovably in the handpiece or in the outer sleeve, preferably on the shared guide element of the adjusting and fixation element.

The locking device, in particular the first locking part or the second locking part comprises, for example, a protrusion or extension which can be accommodated in a receptacle or removed from it. The receptacle preferably comprises at least one resilient or elastically flexible component, for example, a spring arm which is preferably provided with a lug for holding the protrusion. The receptacle, in particular the at least one spring arm, further comprises, for example, a bearing surface for supporting or bearing the protrusion, wherein the bearing surface is preferably provided on a free end of the receptacle or of the spring arm. The protrusion is preferably provided on the actuating element. The receptacle is preferably provided on a component arranged immovably in the handpiece or in the outer sleeve, preferably on the shared guide element of the adjusting and fixation element.

According to one embodiment, the tool-holding sleeve and the driveshaft are connected to one another by an eccentric gear. The eccentric gear preferably comprises an eccentric pin which is provided in particular on the driveshaft of the handpiece, and a groove for receiving the eccentric pin which is provided in particular on the outer surface or on the outer lateral surface of the tool-holding sleeve.

According to one embodiment, the handpiece comprises a handpiece head in which the tool-holding sleeve is arranged so that the central axis of the tool-holding sleeve runs at an angle to an axis of rotation of the driveshaft, wherein further the fixation element, the adjusting element, the actuating element and at least parts of the locking device are also provided on the handpiece head. In particular the shared guidance element, which is designed at least to guide the adjusting element and the fixation element, preferably also for movable support of the actuating element and/or for support of at least a part of the locking device, is provided in the handpiece head.

These and other embodiments will be described below with reference to the following drawings.

DETAILED DESCRIPTION

Figure 1:
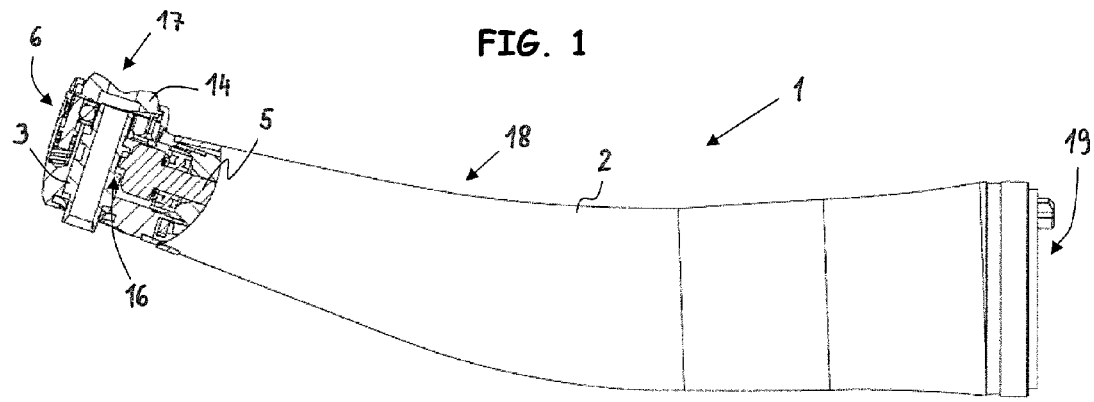
FIG. 1 shows a medical or dental handpiece with a tool-holding sleeve that can be induced to a stroke motion and an adjusting device, which is designed to secure the tool-holding sleeve selectively in a rotational position or to allow a free rotatability of the tool-holding sleeve.

The medical or dental handpiece 1 of FIGS. 1-5 comprises a handpiece head 17 and a handle part 18 connected thereto, preferably a curved or angled handle part 18. An outer sleeve 2 surrounds the handpiece head 17 and the handle part 18. A connecting device 19 which is designed to connect the handpiece 1 to a drive device, for example, a motor, in particular an electric motor is provided at one end of the handpiece 1. One or more driveshafts 5 extend from the connecting device 19 through the handle part 18 in the direction of the handpiece head 17. The connecting device 19 is preferably also designed for connecting the handpiece 1 to a source of power, light or fluid.

A tool-holding sleeve 3, which is designed for detachable accommodation of a treatment tool, in particular a tool having a flat working section, for example, a file 17, is provided in the handpiece head 17. The tool-holding sleeve 3 is connected to the at least one driveshaft 5 by an eccentric gear 16 which is designed to transfer a rotational movement transferred by the driveshaft 5 to the tool-holding sleeve 3 in such a way that the tool-holding sleeve 3 can be induced to a stroke movement. The eccentric gear 16 comprises an eccentric pin provided on the driveshaft 5 and a groove 20 surrounding the outer surface of the tool-holding sleeve 3 in the form of a ring for engagement of the eccentric pin. The tool-holding sleeve 3 is supported in the handpiece 1 by means of at least one sliding bearing 21.

A tool receptacle opening 22 through which the treatment tool can be inserted into or removed from the handpiece head 17 or the tool-holding sleeve 3 is provided on the handpiece head 17. The tool-holding sleeve 3 is arranged in the handpiece head 17 in the tool receptacle opening 22 or adjacent to the tool receptacle opening 22 such that its central axis 4 extends at an angle to an axis of rotation of the driveshaft 5. The tool receptacle opening 22 is thus provided on one side of the handpiece head 17. A sealing device 29, for example, an elastic sealing ring which prevents ingress of contaminants into the handpiece 1 is provided on the tool receptacle opening 22 or around the tool-holding sleeve 3.

The tool-holding sleeve 3 is mounted in the handpiece 1 to rotate about an axis of rotation or a central axis 4 of the tool-holding sleeve 3, so that a treatment tool which is accommodated in the tool-holding sleeve 3 can be arranged in different angles of rotation or different rotational positions. An adjusting device 6 is provided on the handpiece 1 for selective fixation of the tool-holding sleeve 3 or of the treatment tool accommodated therein in a certain rotational position or, alternatively, for free rotation of the tool-holding sleeve 3 or the treatment tool accommodated therein. For actuation of the adjusting device 6 an actuating element 14 is provided on the handpiece head 17, this actuating element being provided in particular on the side of the handpiece head 17, which is opposite the side of the handpiece head 17 with the tool receptacle opening 22.

The actuating element 14 comprises a pushbutton or a key button which is arranged pivotably on the handpiece head 17. The actuating element 14 protrudes in particular through an opening in the cap 23 which is detachably connected to the outer sleeve 2, for example, by means of a thread and/or is designed as part of the outer sleeve 2.

The adjusting device 6 comprises an adjusting element 8 in the form of an elongated, preferably cylindrical pin which extends along a longitudinal axis 10 and a fixation element 7 in the form of a ball. The adjusting element 8 has a first section with a first large outside diameter 11A, a second section with a second small outside diameter 11B and a connecting section 11C which is designed obliquely to the longitudinal axis 10 of the adjusting element 8 and which connects the first and the second sections (see in particular FIG. 3). In addition, the adjusting element 8 is prestressed by a spring element 12 in the form of a spiral spring. The spring element 12 is accommodated in a borehole 24 in the handpiece 1, in particular in the outer sleeve 2 and is supported on a flange 25 of the adjusting element 8 (see FIG. 2).

Figure 2:
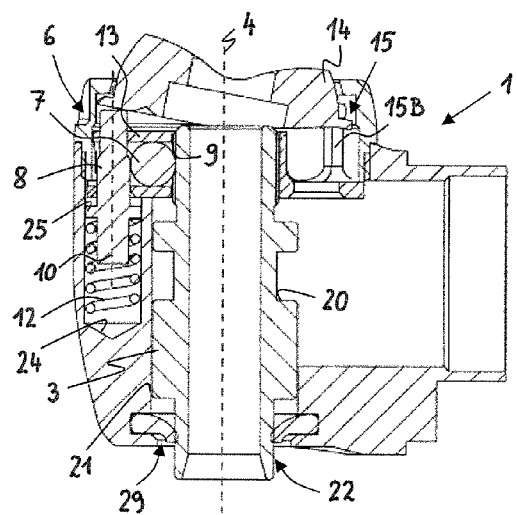
FIG. 2 shows an enlarged diagram of the handpiece head of the handpiece of FIG. 1, wherein the adjusting device assumes a first position in which the tool-holding sleeve is secured in a rotational position.
Figure 3:
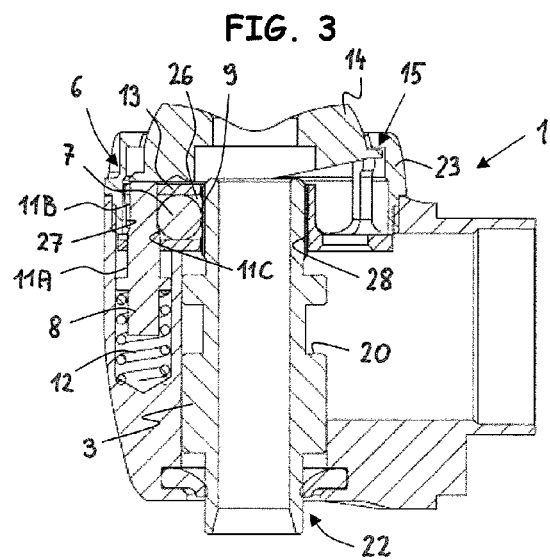
FIG. 3 shows an enlarged diagram of the handpiece head of the handpiece of FIG. 1, in which the adjusting device assumes a second position in which the tool-holding sleeve is freely rotatable.
Figure 4:
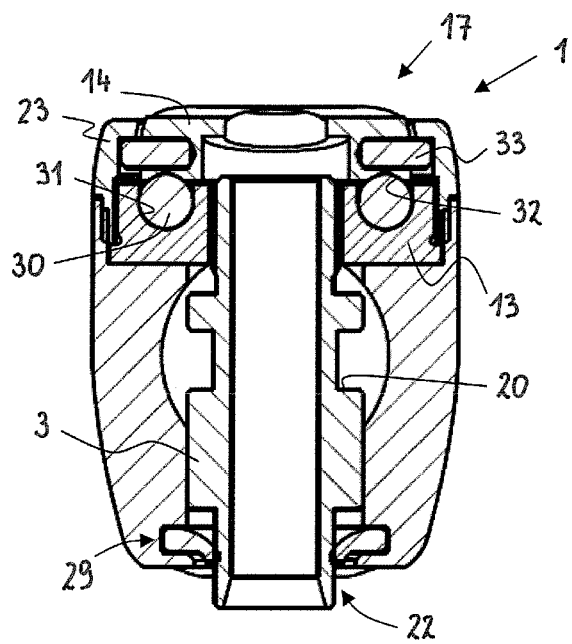
FIG. 4 shows another sectional diagram through the handpiece head of the handpiece of FIG. 1, in which the sectional plane is rotated by 90° with respect to FIGS. 2 and 3.
Figure 5:
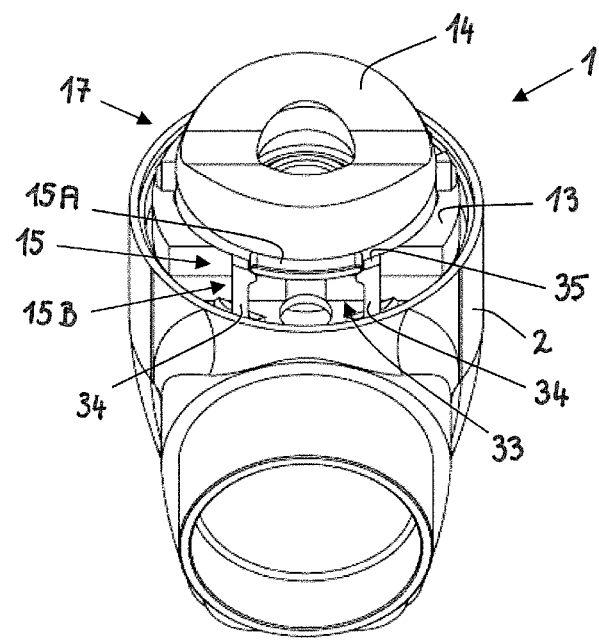
FIG. 5 shows the handpiece head of the handpiece of FIG. 1 in a view from above with an actuating element for the adjusting device and with a locking device for the actuating element and/or the adjusting device.

As shown by a comparison of the two FIGS. 2 and 3, the adjusting element 8 is displaceable along its longitudinal axis 10 substantially parallel to the central axis 4 of the tool-holding sleeve 3 such that either the first large outside diameter 11A or the second small outside diameter 11B is opposite the fixation element 7 or is operatively assigned to it. The latter occurs when the spring element 12 is compressed and the adjusting element 8 is shifted against the spring force of the spring element 12 in the direction of the tool receptacle opening 22. Due to the automatic expansion of the spring element 12 out of the compressed position, the adjusting element 8 is moved away from the tool receptacle opening 22.

If the first large outside diameter 11A is opposite the fixation element 7, then the adjusting element 8, in particular the first section with a first large outside diameter 11A contacts the fixation element 7, in particular such that the fixation element 7 engages a groove-shaped or channel-shaped, preferably concave recess 9 on the outside of the tool-holding sleeve 3 or the fixation element 7 is clamped between the tool-holding sleeve 3 and the adjusting element 8 (see FIG. 2). Thus the tool-holding sleeve 3 and a tool accommodated therein are secured in a rotational position. If the second small outside diameter 11B is opposite the fixation element 7, then the fixation element 7 has space to move away from the tool-holding sleeve 3 or in the direction of the adjusting element 8, in particular such that the fixation element 7 does not engage in the groove-shaped or channel-shaped recess 9 on the outside of the tool-holding sleeve 3 or the fixation element 7 is not clamped between the tool-holding sleeve 3 and the adjusting element 8 (see FIG. 3). The tool-holding sleeve 3 and a tool accommodated therein are thus able to rotate freely. The recess 9 is preferably shaped in the outside or in the outer lateral surface of the tool-holding sleeve 3.

Figure 6A:
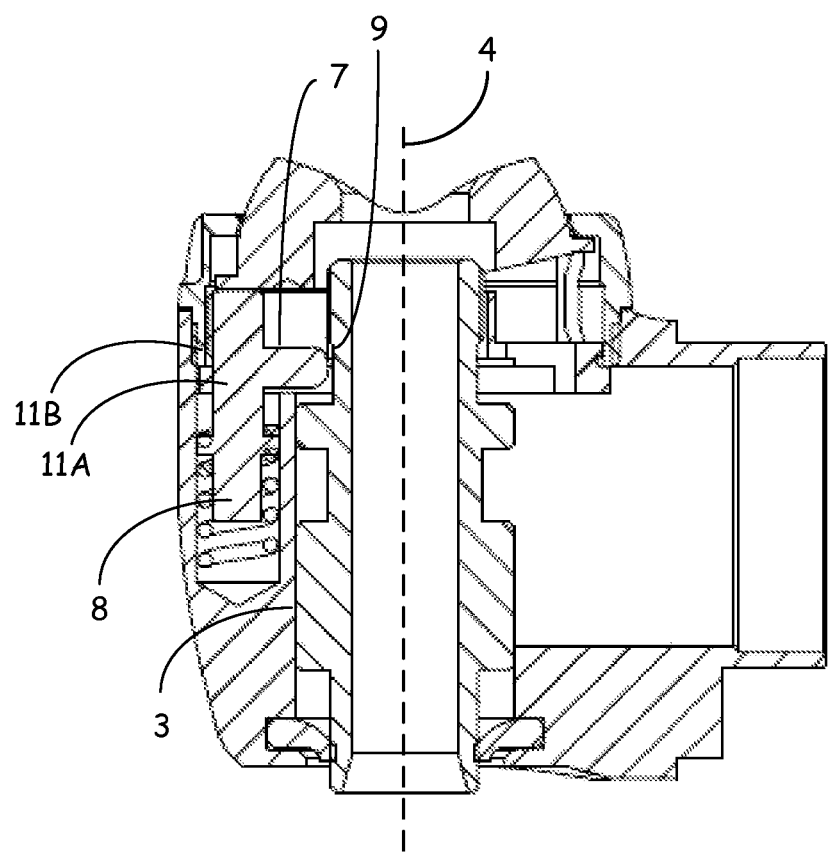
FIGS. 6A and 6B show enlarged sectional diagrams of the handpiece head according to another embodiment in which the fixation element is formed as a pin-shaped extension from the adjusting element and is moveable with the adjusting element parallel to the central axis.
Figure 6B:
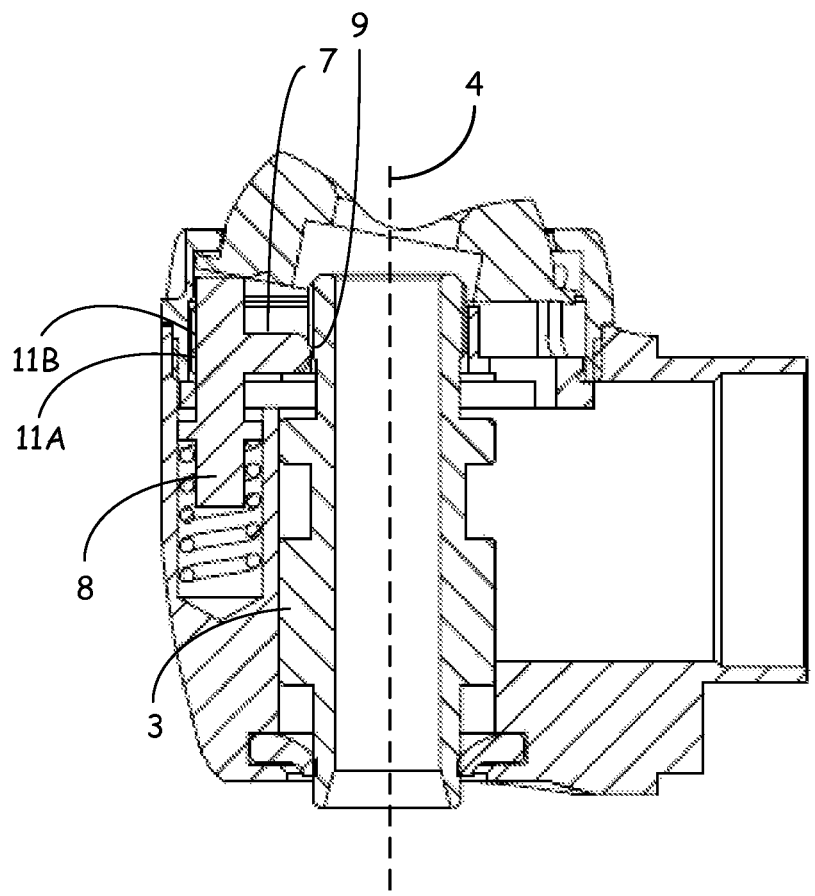

According to an alternative embodiment shown in FIGS. 6A and 6B, the fixation element 7 is formed by a section which is provided on the adjusting element 8 and is movable together with the adjusting element 8 substantially parallel to the central axis 4 of the tool-holding sleeve 3. This section is preferably designed to engage selectively the at least one recess 9 (see FIG. 6B), preferably having a concave shape, on the outside surface of the tool-holding sleeve 3.

Figure 6C:
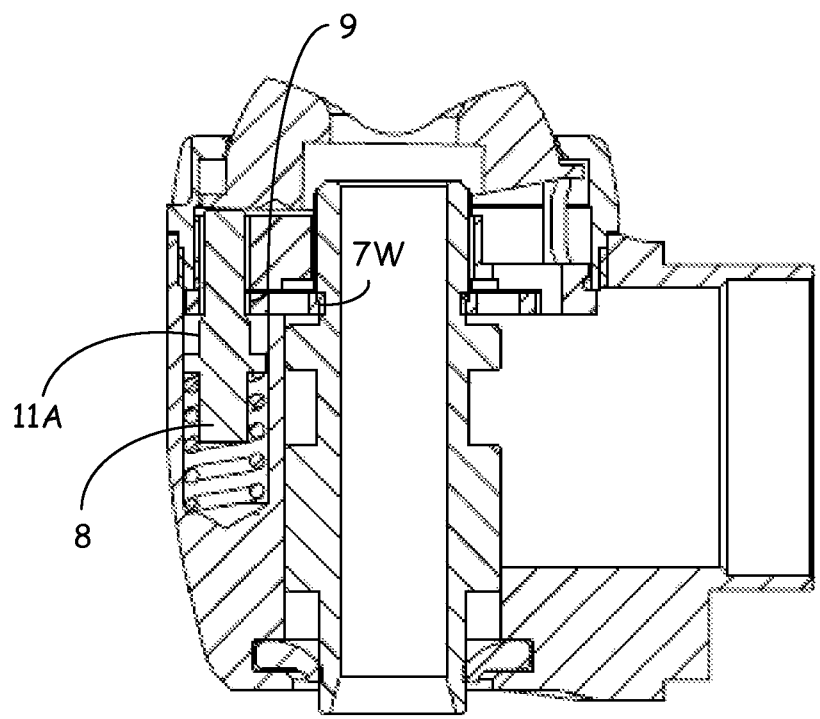
FIGS. 6C and 6D show enlarged sectional diagrams of the handpiece head according to another embodiment in which a large diameter section of the adjusting element engages with a washer.
Figure 6D:
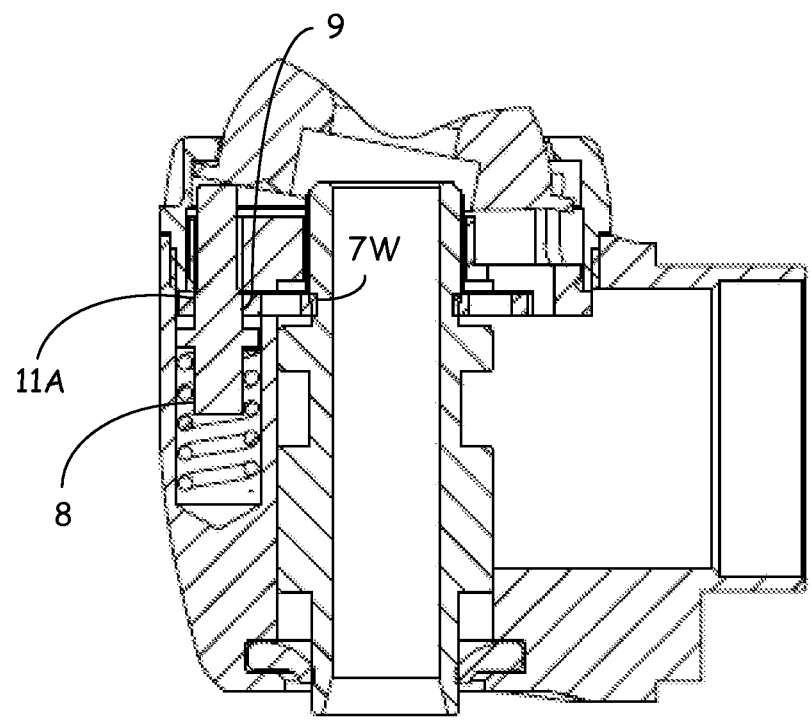

Alternatively, as shown in FIGS. 6C and 6D, the section having the larger diameter (for example, the first section 11A) is designed to engage selectively a recess 9, preferably having a concave shape, wherein the recess is disposed on a component 7W which is connected to the tool-holding sleeve 3 in a rotationally fixed manner. This component 7W is designed as a washer, for example, which comprises at least one recess 9 on its outside circumference to receive the first section 11A and a borehole, which is preferably polygonal and in which the tool-holding sleeve 3 can be or is accommodated. Moreover, the selective fixation or free rotation of the tool-holding sleeve 3 and a tool accommodated therein is as described above, i.e., by shifting the adjusting element 8 together with the first section 11A, so that it optionally engages or does not engage the recess.

The fixation element 7 and the adjustment element 8 are arranged in particular in a shared guide element 13. The shared guide element 13 comprises a first borehole 26 (see FIG. 3) in which the fixation element 7 is movably supported, in particular being radially movable in relation to the central axis 4 of the tool-holding sleeve 3. The shared guide element 13 comprises a second borehole 27, in which the adjusting element 8 is movably accommodated, in particular along its longitudinal axis 10 and substantially parallel to the central axis 4. The boreholes 26, 27 are arranged substantially at right angles to one another. A third borehole 28 in the shared guide element 13 is designed to receive at least a section of the tool-holding sleeve 3, in particular to receive the section of the tool-holding sleeve 3 having the recesses 9. The three boreholes 26, 27, 28 are interconnected. The shared guide element 13 is mounted in the handpiece 1 or the handpiece head 17, in particular on the outer sleeve 2, in a rotationally fixed manner.

The actuating element 14 arranged movably in the handpiece 1 is movably supported in the handpiece 1 due to at least one bearing element 30, in particular pivotably supported. The bearing element 30 comprises, for example, one or more balls which are arranged in receptacles 31 in the handpiece 1. The receptacles 31 are provided, for example, in the shared guide element 13 and in particular are designed so that a portion of the bearing element 30 protrudes out of the receptacle 31 and supports the actuating element 14 (see FIG. 4). Receptacles or setbacks 32 are preferably provided in the actuating element 14, such that the portion of the bearing element 30 protruding beyond the shared guide element 13 engages these receptacles or setbacks 32. Further, two pins 33 which are provided as the axis of rotation or pivot axis of the actuating element 14 are provided on the actuating element 14. The adjusting device 6, in particular the adjusting element 8 is operatively and/or directly connected to the actuating element 14. A movement of the actuating element 14 can thus be transferred to the adjusting device 6, in particular the adjustment element 8, so that the adjusting element 8 is displaceable along its longitudinal axis 10 and, as described above, the tool-holding sleeve 3 and a tool accommodated therein are either secured in a rotational position or are freely rotatable.

A locking device 15 provided on the handpiece 1 is designed to lock the actuating element 14 or the fixation element 7 in a first position, in which the fixation element 7 secures the tool-holding sleeve 3 in one rotational position and/or in a second position, in which the fixation element 7 allows free rotatability of the tool-holding sleeve 3. The locking device 15 comprises a first locking part 15A and a second locking part 15B (see FIG. 5 in particular). The first locking part 15A is provided on the actuating element 14 and comprises a protrusion or projection. The second locking part 15B is provided on the shared guide element 13 and comprises a receptacle 33 in which the first locking part 15A can be accommodated. The receptacle 33 is formed or limited by two resilient or elastically flexible spring arms 34, each preferably being provided with a lug for holding the first locking part 15A (see also FIG. 2). The receptacle 33, in particular the spring arms 34, are provided on or attached to the shared guide element 13. The receptacle 33, in particular the spring arms 34, further comprise(s) a bearing face 35 for supporting or bearing the first locking part 15A (see FIG. 5).

The locking device 15 is thus designed to hold or lock the actuating element 14 and thus the adjusting device 6 in two positions which correspond to the positions illustrated in FIGS. 2 and 3 and described above. In one position the first large outside diameter 11A of the adjusting element 8 is opposite the fixation element 7 or is operatively assigned to the fixation element 7 so that the tool-holding sleeve 3 and a tool accommodated therein are secured in a rotational position (see FIG. 2). In the other position, the second smaller outside diameter 11B of the adjusting element 8 is opposite the fixation element 7 or is operatively assigned to the fixation element 7, so that the tool-holding sleeve 3 and a tool accommodated therein are freely rotatable (see FIG. 3).

The application is not limited to the embodiments described here but instead includes all embodiments which apply or comprise the basic appropriate function principal of the invention. In addition all of the features of all the embodiments described and illustrated here can be combined with one another.

What is claimed is:

1. A medical or dental handpiece, comprising:
an outer sleeve,
a tool-holding sleeve for holding a treatment tool, the tool-holding sleeve being arranged in the outer sleeve, wherein the tool-holding sleeve comprises a central axis about which the tool-holding sleeve can be rotated and wherein the tool-holding sleeve can be induced to a stroke motion by a driveshaft of the handpiece, and
an adjusting device, which is configured to secure the tool-holding sleeve selectively in a rotational position or to allow a free rotatability of the tool-holding sleeve, wherein
the adjusting device comprises a fixation element, which secures or releases the tool-holding sleeve and an adjusting element, which is at least operatively connected to the fixation element, wherein
the adjusting element comprises an elongate pin which is movable substantially parallel to the central axis of the tool-holding sleeve, wherein
the elongate pin has a first section with a first outside dimension and a second section with a second outside dimension being different from said first outside dimension, wherein
the elongate pin is movable substantially parallel to the central axis of the tool-holding sleeve relative to a contact area on or adjacent to the tool-holding sleeve, such that, in a first position, one of the first section with the first outside dimension and the second section with the second outside dimension is arranged opposite the contact area, and in a second position, the other of the first section and the second section is arranged opposite the contact area, such that, in one of the first position and the second position, the tool-holding sleeve is secured in a rotational position, and in the other of the first position and the second position, the tool-holding sleeve is allowed to freely rotate.

2. The medical or dental handpiece according to claim 1, wherein the fixation element comprises at least one securing element that is movable substantially radially relative to the central axis of the tool-holding sleeve.

3. The medical or dental handpiece according to claim 1, wherein the fixation element is movable between a position in which it contacts the tool-holding sleeve and a position in which it does not contact the tool-holding sleeve.

4. The medical or dental handpiece according to claim 1, wherein the fixation element comprises a section which is provided on the adjusting element and is movable together with the adjusting element substantially parallel to the central axis of the tool-holding sleeve.

5. The medical or dental handpiece according to claim 1, wherein the contact area comprises at least one recess for receiving the fixation element on an outside surface of the tool-holding sleeve or on a component rotationally fixed to the tool-holding sleeve.

6. The medical or dental handpiece according to claim 1, wherein the two sections of the adjusting element which have different outside dimensions are connected to one another by a connecting section of the adjusting element arranged obliquely to the longitudinal axis of the adjusting element.

7. The medical or dental handpiece according to claim 1, comprising a spring element prestressing the adjusting element.

8. The medical or dental handpiece according to claim 1, comprising a shared guide element arranged in the outer sleeve and designed to guide the adjusting element and the fixation element.

9. The medical or dental handpiece according to claim 1, comprising an actuating element for actuating the adjusting device, wherein the actuating element is movable in relation to the outer sleeve of the handpiece.

10. The medical or dental handpiece of claim 9, wherein the actuating element is rotatable in relation to the outer sleeve of the handpiece.

11. The medical or dental handpiece of claim 9, wherein the actuating element is pivotable in relation to the outer sleeve of the handpiece.

12. The medical or dental handpiece according to claim 1, comprising a locking device which is designed to lock the actuating element or the fixation element at least in a first position in which the fixation element secures the tool-holding sleeve in a rotational position or in a second position in which the fixation element allows free rotatability of the tool-holding sleeve.

13. The medical or dental handpiece according to claim 12, wherein the locking device comprises a first locking part on the actuating element and a second locking part, wherein the first locking part and the second locking part are movable in relation to one another by the movement of the actuating element.

14. The medical or dental handpiece according to claim 1, wherein the handpiece comprises a handpiece head in which the tool-holding sleeve is arranged such that the central axis of the tool-holding sleeve runs at an angle to an axis of rotation of the driveshaft and wherein the fixation element, the adjusting element and the actuating element are provided on the handpiece head.

15. The medical or dental handpiece according to claim 1, wherein the fixation element comprises a spheroidal section.

16. The medical or dental handpiece according to claim 1, wherein the fixation element comprises a ball.

17. A medical or dental handpiece, comprising:
an outer sleeve,
a tool-holding sleeve for holding a treatment tool, the tool-holding sleeve being arranged in the outer sleeve, wherein the tool-holding sleeve comprises a central axis about which the tool-holding sleeve can be rotated and wherein the tool-holding sleeve can be induced to a stroke motion by a driveshaft of the handpiece, and an adjusting device, which is configured to secure the tool-holding sleeve selectively in a rotational position or to allow a free rotatability of the tool-holding sleeve, wherein the adjusting device comprises an elongate rod which is movable substantially parallel to the central axis of the tool-holding sleeve, wherein the elongate rod has a first section with a first outside dimension and a second section with a second outside dimension being different from said first outside dimension, wherein the elongate rod is movable substantially parallel to the central axis of the tool-holding sleeve relative to a contact area on or adjacent the tool-holding sleeve, such that in a first position, one of the first section with the first outside dimension and the second section with the second outside dimension is arranged opposite the contact area, and in a second position, the other of the first section and the second section is arranged opposite the contact area, such that in one of the first position and the second position, the tool-holding sleeve is secured in a rotational position, and in the other of the first position and the second position, the tool-holding sleeve is allowed to freely rotate.

18. The medical or dental handpiece according to claim 17, wherein the contact area comprises at least one recess on the outside surface of the tool-holding sleeve or a component connected in a rotationally fixed manner to the tool-holding sleeve.

19. A medical or dental handpiece, comprising:

an outer sleeve, a tool-holding sleeve for holding a treatment tool, the tool-holding sleeve being arranged in the outer sleeve, wherein the tool-holding sleeve comprises a central axis about which the tool-holding sleeve can be rotated and wherein the tool-holding sleeve can be induced to a stroke motion by a driveshaft of the handpiece, an adjusting device, which is configured to secure the tool-holding sleeve selectively in a rotational position or to allow a free rotatability of the tool-holding sleeve, wherein the adjusting device comprises an adjusting element, wherein the adjusting element is movable substantially parallel to the central axis of the tool-holding sleeve, an actuating element for actuating the adjusting element parallel to the central axis of the tool-holding sleeve, wherein the actuating element is pivotable in relation to the outer sleeve of the handpiece, and a locking device which is designed to lock the actuating element at least in a first pivoted position in which the adjusting device secures the tool-holding sleeve in a rotational position or in a second pivoted position in which the adjusting device allows free rotatability of the tool-holding sleeve.

* * * * *